(12) United States Patent
Ishikawa et al.

(10) Patent No.: US 11,037,686 B2
(45) Date of Patent: Jun. 15, 2021

(54) INFORMATION PROCESSING APPARATUS, INFORMATION PROCESSING METHOD, AND INFORMATION PROCESSING PROGRAM

(71) Applicant: FUJIFILM CORPORATION, Tokyo (JP)

(72) Inventors: Shigetoshi Ishikawa, Kanagawa (JP); Yasuhisa Kaneko, Kanagawa (JP); Haruyasu Nakatsugawa, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 0 days.

(21) Appl. No.: 16/736,838

(22) Filed: Jan. 8, 2020

(65) Prior Publication Data
US 2020/0265960 A1    Aug. 20, 2020

(30) Foreign Application Priority Data
Feb. 18, 2019   (JP) .............................. JP2019-026961

(51) Int. Cl.
*G16H 50/80* (2018.01)
*G16H 50/30* (2018.01)
*G08B 21/02* (2006.01)

(52) U.S. Cl.
CPC ............. *G16H 50/80* (2018.01); *G08B 21/02* (2013.01); *G16H 50/30* (2018.01)

(58) Field of Classification Search
CPC .................................................... G16H 50/30
See application file for complete search history.

(56) References Cited

U.S. PATENT DOCUMENTS

| | | | | |
|---|---|---|---|---|
| 5,543,131 A | * | 8/1996 | Levy | A01K 67/027 424/9.2 |
| 9,538,729 B2 | * | 1/2017 | Yarden | A01K 11/004 |
| 10,275,526 B2 | * | 4/2019 | Dodge | G06F 16/951 |
| 10,418,133 B2 | * | 9/2019 | Arora | G06Q 10/10 |
| 10,669,592 B2 | * | 6/2020 | Freeman-Cook | C12Q 1/689 |
| 10,765,091 B2 | * | 9/2020 | Miyahara | G06Q 10/06311 |

(Continued)

FOREIGN PATENT DOCUMENTS

JP    2011-248802 A    12/2011

*Primary Examiner* — K. Wong
(74) *Attorney, Agent, or Firm* — Solaris Intellectual Property Group, PLLC

(57) ABSTRACT

An information processing apparatus, an information processing method, and an information processing program which are capable of suppressing an increase in consumption of system resources used for suppressing a spread of an infection disease are acquired. An information processing apparatus includes an acquisition unit that acquires information regarding an infection disease of a first animal infected with the infection disease, a specification unit that specifies a second animal positioned within a behavior area of the first animal, a determination unit that determines whether or not the infection disease of the first animal is likely to infect the second animal, and a notification unit that notifies an owner of the second animal of an alarm regarding the infection disease in a case where it is determined that the infection disease of the first animal is likely to infect the second animal.

11 Claims, 9 Drawing Sheets

(56) References Cited

U.S. PATENT DOCUMENTS

| | | | | |
|---|---|---|---|---|
| 2002/0059030 A1* | 5/2002 | Otworth | ............. | A61B 5/411 |
| | | | | 702/19 |
| 2002/0103671 A1* | 8/2002 | Pederson | ........ | G06Q 10/0635 |
| | | | | 705/2 |
| 2012/0029260 A1* | 2/2012 | Garsd | ............. | A61K 49/0008 |
| | | | | 600/1 |
| 2013/0222141 A1* | 8/2013 | Rhee | ................ | G16H 50/80 |
| | | | | 340/573.3 |

* cited by examiner

FIG. 3

| OWNER INFORMATION | | | | ANIMAL INFORMATION | | | | | | |
|---|---|---|---|---|---|---|---|---|---|---|
| ID | NAME | CONTACT INFORMATION | ... | ID | NAME | GENDER | AGE | RACE | BREED | ... |
| A100 | AAA | aaa@bbb | ... | B100 | TARO | MALE | 7 | DOG | CHIHUAHUA | ... |
| | | | ... | B101 | JIRO | MALE | 4 | DOG | POODLE | ... |
| | | | ... | ... | ... | ... | ... | ... | ... | ... |
| A101 | BBB | ccc@ddd | ... | B105 | HANA | FEMALE | 3 | CAT | PERSIAN | ... |
| ... | ... | ... | ... | ... | ... | ... | ... | ... | ... | ... |

FIG. 4

| ID | DATE AND TIME | POSITIONAL INFORMATION |
|---|---|---|
| B100 | 12/1/2018 10:00:00 | 35.700001N 139.700001E |
| | 12/1/2018 10:00:10 | 35.700002N 139.700002E |
| | ... | ... |
| B101 | ... | ... |
| ... | ... | ... |

FIRST ANIMAL

SECOND ANIMAL

INFORMATION PROCESSING APPARATUS, INFORMATION PROCESSING METHOD, AND INFORMATION PROCESSING PROGRAM

CROSS-REFERENCE TO RELATED APPLICATION

This application claims priority under 35 USC 119 from Japanese Patent Application No. 2019-026961 filed Feb. 18, 2019, the disclosure of which is incorporated by reference herein.

BACKGROUND

Technical Field

The present disclosure relates to an information processing apparatus, an information processing method, and an information processing program.

Related Art

An infection monitoring system that notifies participants in the system that the participants are suspected of being infected with a virus is disclosed (see JP2011-248802A). The infection monitoring system acquires an infection estimation date and time which is a date and time when it is estimated that a person infected with a virus is infected with the virus from a hospital. The infection monitoring system performs the aforementioned notification for the participants closes to the infected person within a predetermined distance after the infection estimation date and time.

SUMMARY

For example, in a technology for notifying an owner of a second animal close to a first animal infected with an infection disease of an alarm regarding the infection disease, in a case where the first animal stays in a place in which a plurality of animals gathers, there is a plurality of owners as notification targets. As stated above, in a case where the notification targets are simply determined by only a distance, there are too many notification targets, and thus, the consumption of system resources used for suppressing a spread of the infection disease is increased. In the technology described in JP2011-248802A, it is not considered that the consumption of the system resources is increased.

The present disclosure has been made in view of the aforementioned circumstances, and an object of the present disclosure is to provide an information processing apparatus, an information processing method, and an information processing program which are capable of suppressing an increase in consumption of system resources used for suppressing a spread of an infection disease.

In order to achieve the object, an information processing apparatus of the present disclosure comprises an acquisition unit that acquires information regarding an infection disease of a first animal infected with the infection disease, a specification unit that specifies a second animal positioned within a behavior area of the first animal, a determination unit that determines whether or not the infection disease of the first animal is likely to infect the second animal, and a notification unit that notifies an owner of the second animal of an alarm regarding the infection disease in a case where it is determined that the infection disease of the first animal is likely to infect the second animal.

In the information processing apparatus of the present disclosure, the determination unit may determine whether or not the infection disease of the first animal is likely to infect the second animal by determining whether or not a race of the second animal is a race of an animal that is likely to be infected with the infection disease of the first animal.

In the information processing apparatus of the present disclosure, in a case where there is a plurality of the first animals, the specification unit may specify, as a zone in which there is an infection source of the infection disease, a zone common to the behavior areas of the plurality of first animals, and may specify, as the second animal, the animal positioned within the specified zone.

In the information processing apparatus of the present disclosure, the specification unit may specify the second animal positioned within the behavior area of the first animal during a lifetime of a virus of the infection disease of the first animal.

In the information processing apparatus of the present disclosure, the determination unit may further determine whether or not the infection disease of the first animal is likely to infect human, and in a case where it is further determined that the infection disease of the first animal is likely to infect human, the notification unit may further notify the owner of the second animal of an alarm indicating that the infection disease is likely to infect human.

In the information processing apparatus of the present disclosure, the notification unit may notify of the alarm regarding the infection disease by changing a content of the alarm depending on a degree of overlapping of a movement path of the first animal and a movement path of the second animal.

In order to achieve the object, an information processing method of the present disclosure is executed by a computer. The method comprises acquiring information regarding an infection disease of a first animal infected with the infection disease, specifying a second animal positioned within a behavior area of the first animal, determining whether or not the infection disease of the first animal is likely to infect the second animal, and notifying an owner of the second animal of an alarm regarding the infection disease in a case where it is determined that the infection disease of the first animal is likely to infect the second animal.

In order to achieve the object, an information processing program of the present disclosure causes a computer to execute processes of acquiring information regarding an infection disease of a first animal infected with the infection disease, specifying a second animal positioned within a behavior area of the first animal, determining whether or not the infection disease of the first animal is likely to infect the second animal, and notifying an owner of the second animal of an alarm regarding the infection disease in a case where it is determined that the infection disease of the first animal is likely to infect the second animal.

An information processing apparatus of the present disclosure comprises a memory that stores a command to be executed on a computer, and a processor that is configured to execute the stored command. The processor acquires information regarding an infection disease of a first animal infected with the infection disease, specifies a second animal positioned within a behavior area of the first animal, determines whether or not the infection disease of the first animal is likely to infect the second animal, and notifies an owner of the second animal of an alarm regarding the infection disease in a case where it is determined that the infection disease of the first animal is likely to infect the second animal.

According to the present disclosure, it is possible to suppress an increase in consumption of system resources used for suppressing a spread of an infection disease.

BRIEF DESCRIPTION OF THE DRAWINGS

Exemplary Embodiments of the present disclosure will be described in detail with reference to the following figures, wherein:

FIG. 3 is a diagram showing an example of an animal management table according to the embodiment.

FIG. 4 is a diagram showing an example of a movement history table according to the embodiment.

DETAILED DESCRIPTION

Hereinafter, form examples for implementing a technology of the present disclosure will be described in detail.

Figure 1:
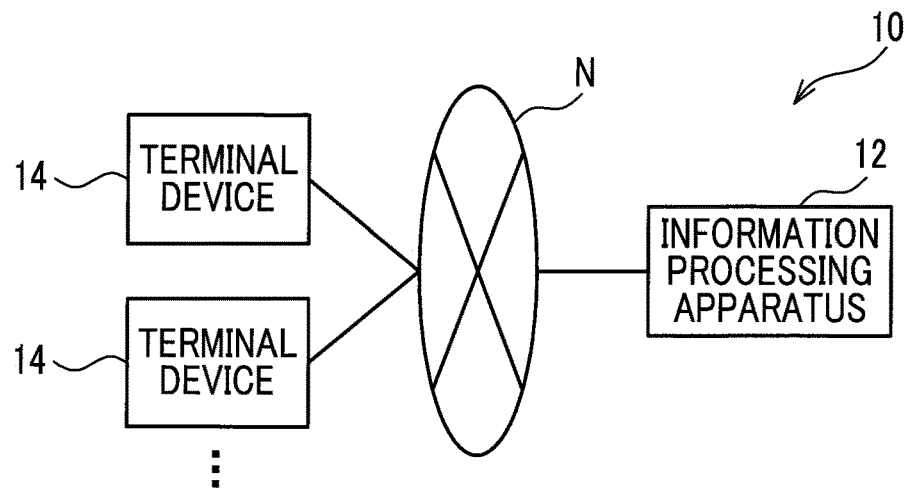
FIG. 1 is a block diagram showing an example of a configuration of an information processing system according to an embodiment.

Initially, a configuration of an information processing system 10 according to the present embodiment will be described with reference to FIG. 1. As shown in FIG. 1, the information processing system 10 includes an information processing apparatus 12 and a plurality of terminal devices 14. The information processing apparatus 12 and the plurality of terminal devices 14 are connected to a network N, and can communicate with each other via the network N.

For example, the information processing apparatus 12 is provided in an animal hospital. Examples of the information processing apparatus 12 include a server computer. The information processing apparatus 12 may be a cloud server. For example, the terminal device 14 is owned by an owner of an animal such as a pet. Examples of the terminal device 14 include a smartphone and a tablet computer. The "animal" in the present specification means an animal such as a dog and a cat except for "human".

Figure 2:
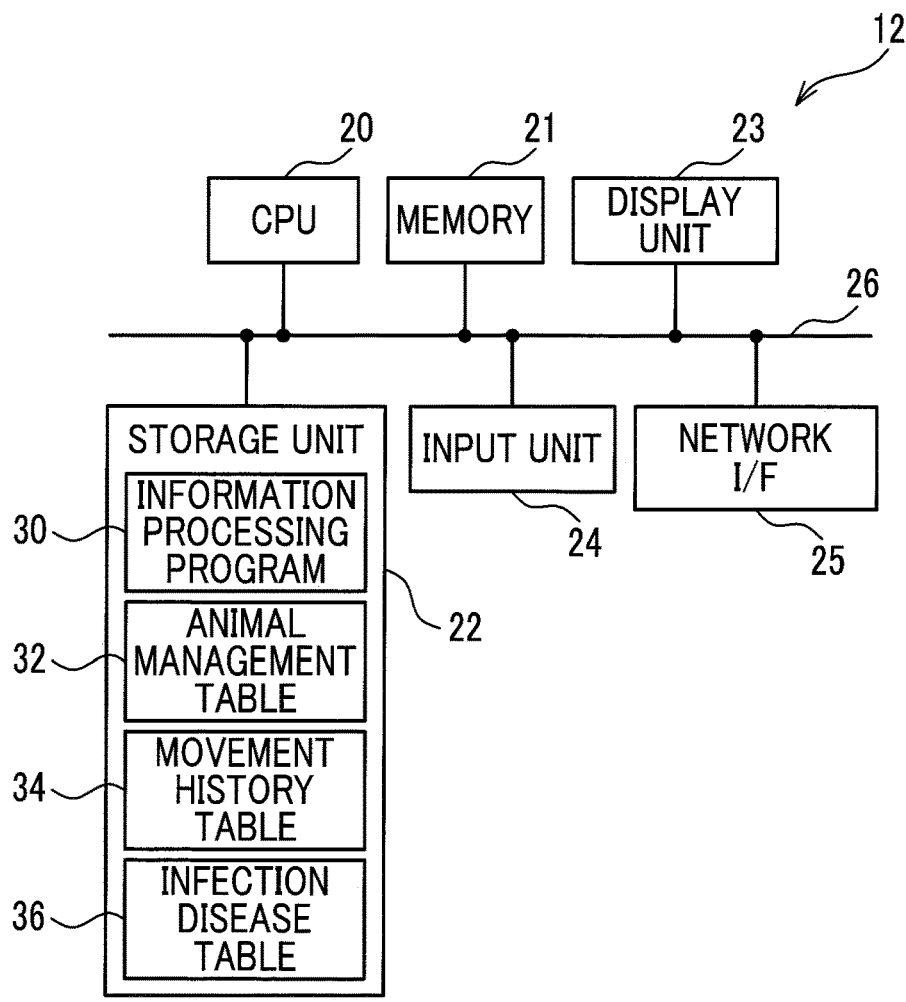
FIG. 2 is a block diagram showing an example of a hardware configuration of an information processing apparatus according to the embodiment.

Next, a hardware configuration of the information processing apparatus 12 according to the present embodiment will be described with reference to FIG. 2. As shown in FIG. 2, the information processing apparatus 12 includes a central processing unit (CPU) 20, a memory 21 as a temporary storage region, and a nonvolatile storage unit 22. The information processing apparatus 12 includes a display unit 23 such as a liquid crystal display, an input unit 24 such as a keyboard and a mouse, and a network interface (I/F) 25 connected to the network N. The CPU 20, the memory 21, the storage unit 22, the display unit 23, the input unit 24, and the network I/F 25 are connected to a bus 26.

The storage unit 22 is implemented by a hard disk drive (HDD), a solid state drive (SSD), and a flash memory. An information processing program 30 is stored in the storage unit 22 as a storage medium. The CPU 20 reads out the information processing program 30 from the storage unit 22, develops the readout information processing program into the memory 21, and executes the developed information processing program 30.

An animal management table 32, a movement history table 34, and an infection disease table 36 are stored in the storage unit 22.

FIG. 3 shows an example of the animal management table 32. The animal management table 32 is a table for managing owners of animals and animals raised by the owners. As shown in FIG. 3, information (hereinafter, referred to as "owner information") regarding the owner of the animal and information (hereinafter, referred to as "animal information") regarding the animal are stored in association with each other in the animal management table 32.

The owner information includes an identifier (ID) as an example of identification information of the owner, a name, and contact information. Although it has been described in the present embodiment that an electronic mail address is applied as the contact information, the present invention is not limited thereto. As the contact information, a messaging service ID may be applied, an account ID of a social networking service (SNS) may be applied, or a telephone number may be applied.

The animal information includes an ID as an example of identification information of the animal raised by the owner indicated by the corresponding owner information, a name, a gender, an age, a race, and a breed. In a case where one owner raises a plurality of animals, a plurality of animal information items is associated with one owner information.

FIG. 4 shows an example of the movement history table 34. The movement history table 34 is a table for ascertaining a behavior area of the animal. As shown in FIG. 4, in the movement history table 34, a date and time and positional information are stored in association with the ID of the animal. As shown in FIG. 4, in the present embodiment, latitude and longitude are stored as the positional information. The positional information of the animal is periodically transmitted to the information processing apparatus 12 by a collar with a Global Positioning System (GPS) module attached to the animal. The information processing apparatus 12 receives the periodically transmitted positional information of the animal, and stores the received positional information in association with the ID of the animal and the reception date and time in the movement history table 34.

Figure 5:
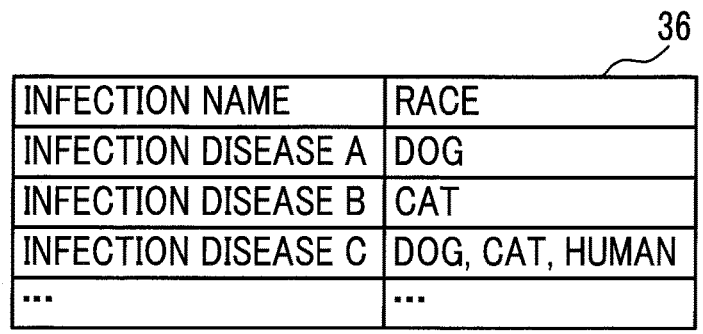
FIG. 5 is a diagram showing an example of an infection disease table according to the embodiment.

FIG. 5 shows an example of infection disease table 36. The infection disease table 36 is a table for managing a target that is likely to be infected with an infection disease. As shown in FIG. 5, in the infection disease table 36, a race of the animal that is likely to be infected with the infection disease is stored for each infection disease. In addition to the animal, "human" in addition to the race of the animal is stored in a race column for an infection disease that is likely to infect human.

Examples of an infection disease that infects only cats include feline panleukopenia, feline leukemia virus infection, feline immunodeficiency virus infection, feline infectious peritonitis, and feline cold. Examples of an infection disease that infects only dogs include canine kennel cough, canine distemper virus infection, canine parvovirus infection, and canine adenovirus infection. Examples of an infection disease that infects both dogs and cats and infects humans include dog and cat roundworm larva migration and dermatophytosis.

Figure 6:
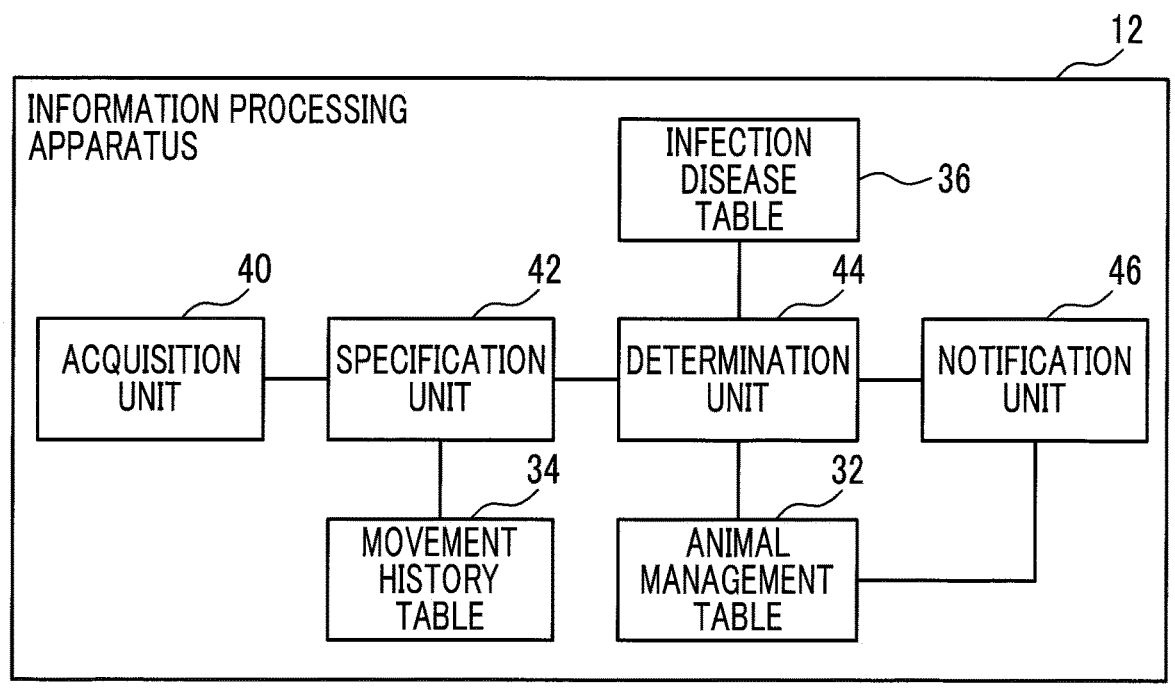
FIG. 6 is a block diagram showing an example of a functional configuration of the information processing apparatus according to the embodiment.

Next, a functional configuration of the information processing apparatus 12 according to the present embodiment will be described with reference to FIG. 6. As shown in FIG. 6, the information processing apparatus 12 includes an acquisition unit 40, a specification unit 42, a determination unit 44, and a notification unit 46. The CPU 20 executes the information processing program 30, and thus, the information processing program functions as the acquisition unit 40, the specification unit 42, the determination unit 44, and the notification unit 46.

In a case where the animal to be diagnosed is suspected of being inspected with the infection disease, a veterinarian of the animal hospital according to the present embodiment requests a diagnosis by collecting a specimen from the animal and transmitting the collected specimen to an external inspection agency. In a case where the inspection in the inspection agency is completed, information indicating an inspection result is transmitted to the information processing apparatus 12 from the inspection agency, and the information processing apparatus 12 receives the information indicating the inspection information transmitted from the external inspection agency. The information indicating the inspection result includes the ID of the animal to be diagnosed, and includes a disease name of the infection disease in a case where the animal is infected with the infection disease. The information indicating the inspection result may be input by the veterinarian of the animal hospital through the input unit 24.

The acquisition unit 40 acquires information (hereinafter, referred to as "infection disease information") regarding the infection disease of the animal (hereinafter, referred to as a "first animal") infected with the infection disease from the received information indicating the inspection result. The infection disease information according to the present embodiment includes the ID of the animal infected with the infection disease and the disease name of the infection disease.

The specification unit 42 specifies, as a behavior area of the first animal, a trajectory of positional information of the first animal after a timing at which the first animal is infected with the infection disease while referring to the movement history table 34. The specification unit 42 specifies an animal (hereinafter, referred to as a "second animal") positioned within the specified behavior area by acquiring the ID of the animal positioned within the specified behavior area within a predetermined period (for example, within three hours) while referring to the movement history table 34. For example, the predetermined period may be a lifetime of a virus of the infection disease that infects the first animal.

The determination unit 44 acquires the race corresponding to the ID of the second animal specified by the specification unit 42 while referring to the animal management table 32. The determination unit 44 determines whether or not the race of the second animal is a race of an animal that is likely to be infected with the infection disease that infects the first animal while referring to the infection disease table 36. Through this determination, the determination unit 44 determines whether or not the infection disease of the first animal is likely to infect the second animal. The determination unit 44 determines whether or not the infection disease that infects the first animal is likely to infect human while referring to the infection disease table 36.

In a case where the determination unit 44 determines that the infection disease of the first animal is likely to infect the second animal, the notification unit 46 acquires the contact information of the owner of the second animal while referring to the animal management table 32. The notification unit 46 notifies the owner of the second animal of an alarm regarding the infection disease by transmitting text data of an alarm regarding the infection disease that infects the first animal to the acquired contact information.

In a case where the determination unit 44 determines that the infection disease of the first animal is likely to infect human, the notification unit 46 transmits the text data of the alarm indicating that the infection disease of the first animal is likely to infect human to the acquired contact information. Through the transmission of the text data of this alarm, the notification unit 46 further notifies the owner of the second animal of the alarm indicating that the infection disease is likely to infect human. The notification unit 46 may notify of the alarm by sound data instead of the text data, or may notify of the alarm by both the text data and the sound data.

Figure 7:
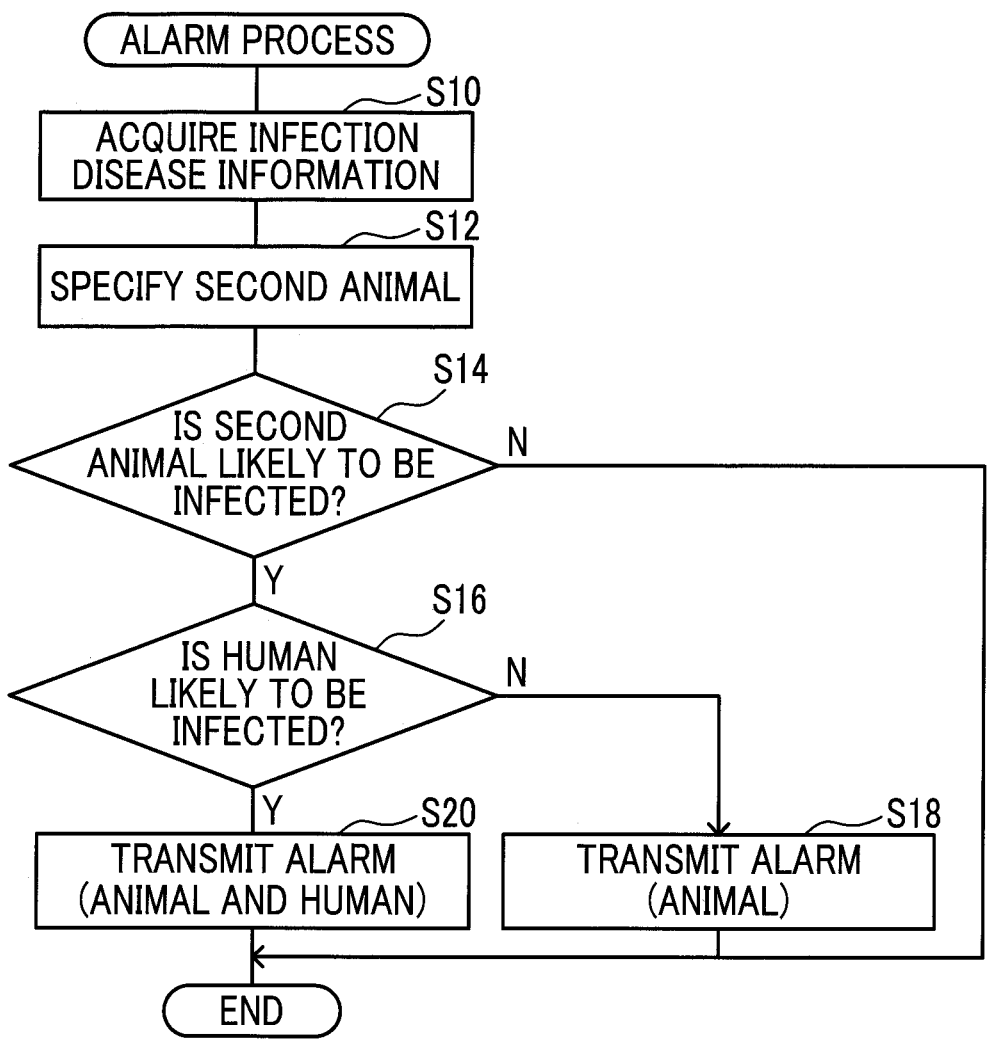
FIG. 7 is a flowchart showing an example of an alarm process according to the embodiment.

Next, the actions of the information processing apparatus 12 according to the present embodiment will be described with reference to FIG. 7. The CPU 20 executes the information processing program 30, and thus, an alarm process shown in FIG. 7 is performed. The alarm process shown in FIG. 7 is performed in a case where the information indicating the inspection result transmitted from the inspection agency is received by the information processing apparatus 12.

In step S10 of FIG. 7, the acquisition unit 40 acquires the infection disease information of the first animal from the received information indicating the inspection result. In step S12, the specification unit 42 specifies the behavior area of the first animal at a timing when it is estimated that the first animal is infected with the infection disease while referring to the movement history table 34. The specification unit 42 specifies the second animal positioned within the specified behavior area as described above while referring to the movement history table 34. In a case where there is a plurality of second animals specified by the specification unit 42, step S14 and subsequent processes to be described below are individually performed for each of the second animals.

In step S14, the determination unit 44 acquires the race corresponding to the ID of the second animal specified through the process of step S12 while referring to the animal management table 32. As stated above, the determination unit 44 determines whether or not the infection disease of the first animal is likely to infect the second animal while referring to the infection disease table 36. In a case where this determination is a positive determination, the process proceeds to step S16.

In step S16, the determination unit 44 determines whether or not the infection disease of the first animal is likely to infect human while referring to the infection disease table 36. In a case where this determination is a negative determination, the process proceeds to step S18.

Figure 8:
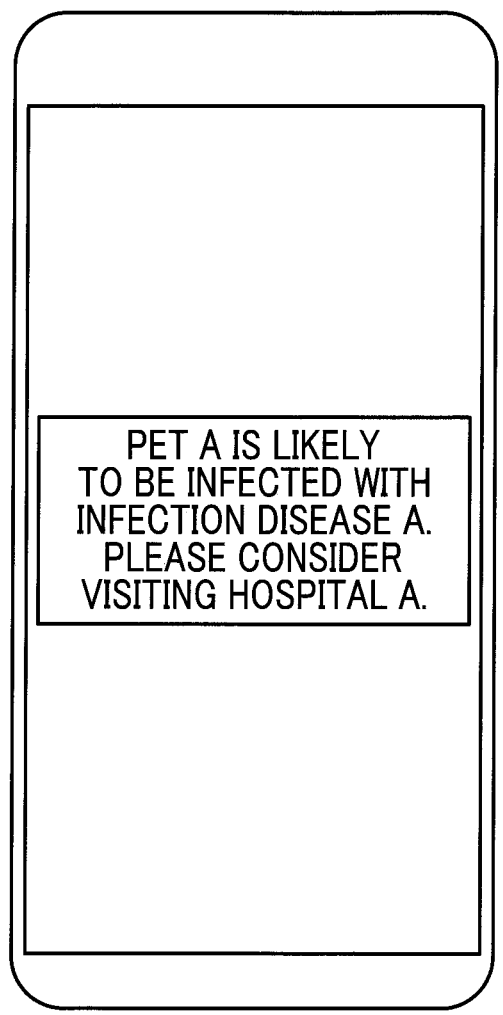
FIG. 8 is a diagram showing an example of a first alarm display screen according to the embodiment.

In step S18, the notification unit 46 acquires the contact information of the owner of the second animal while referring to the animal management table 32 as stated above, and transmits the text data of the alarm regarding the infection disease of the first animal to the acquired contact information. Through the process of step S18, for example, a message indicating that the second animal is likely to be infected with the infection disease and a message for prompting the owner to visit the animal hospital are displayed on a display unit of the terminal device 14 owned by the owner of the second animal, as shown in FIG. 8. In a case where the process of step S18 is ended, the present alarm process is ended.

Figure 9:
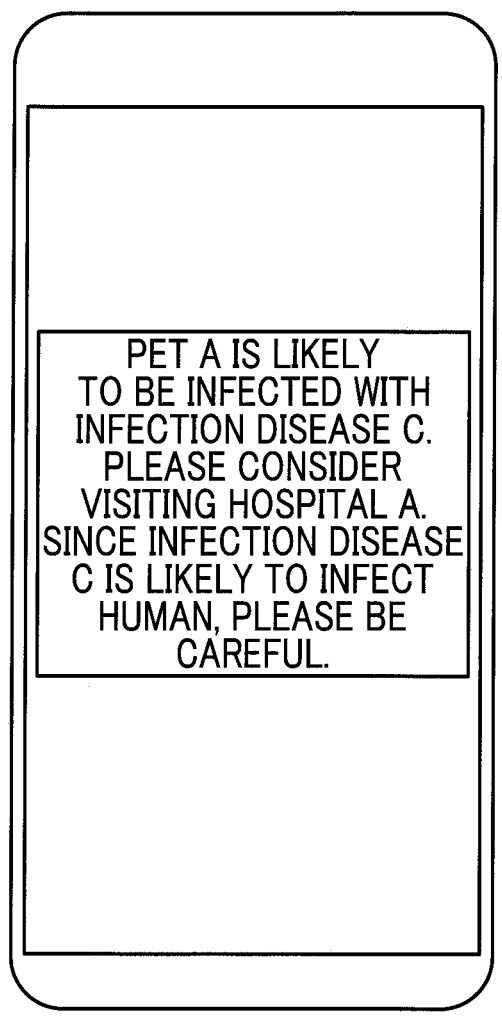
FIG. 9 is a diagram showing an example of a second alarm display screen according to the embodiment.

Meanwhile, in a case where this determination of step S16 is a positive determination, the process proceeds to step S20. In step S20, the notification unit 46 acquires the contact information of the owner of the second animal while referring to the animal management table 32. The notification unit 46 also transmits the text data of the alarm indicating that the infection disease of the first animal is likely to infect human in addition to the same text data as that in step S18 to the acquired contact information. Through the process of step S20, for example, a message indicating that the infection disease is likely to infect human is also displayed in addition to the same message as that in FIG. 8, as shown in FIG. 9. In a case where the process of step S20 is ended, the present alarm process is ended. The present alarm process is ended even in a case where the determination of step S14 is a negative determination.

As described above, according to the present embodiment, in a case where it is determined that the infection disease that infects the first animal is likely to infect the second animal, the alarm regarding the infection disease is notified to the owner of the second animal. Accordingly, it is possible to suppress an increase in consumption of system resources used for suppressing a spread of the infection disease compared to a case where the alarm is notified to the owners of all the animals positioned within the behavior area of the first animal.

According to the present embodiment, in a case where it is determined that the infection disease of the first animal is likely to infect human, the alarm indicating that the infection disease is likely to infect human is further notified to the owner of the second animal. Accordingly, since the owner can ascertain that the owner himself or herself is likely to be infected with the infection disease, the owner himself or herself can suppress the spread of the infection disease, and thus, it is possible to further suppress the spread of the infection disease.

Figure 10:
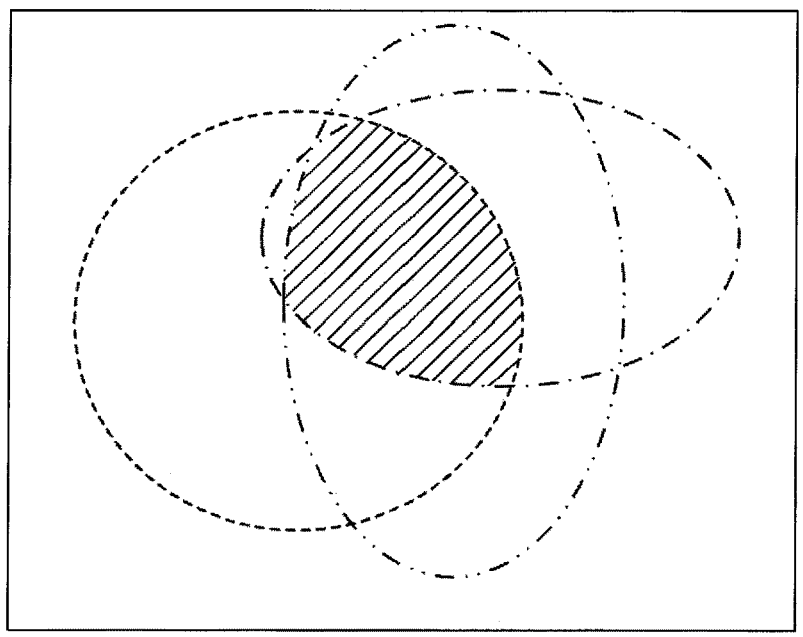
FIG. 10 is a diagram for describing a zone common to behavior areas according to a modification example.

Although it has been described in the embodiment that the specification unit 42 specifies the animal positioned within the behavior area of the first animal, the present invention is not limited thereto. For example, in a case where there is a plurality of first animals infected with the same infection disease as the inspection result received at the same timing, for example, the specification unit 42 may specify, as a zone in which an infection source of the infection disease of the first animal, a zone common to the behavior areas of the plurality of first animals, as shown in FIG. 10. In this case, the specification unit 42 specifies, as the second animal, the animal positioned within the specified zone. In the example of FIG. 10, the behavior areas of three first animals are respectively represented by a broken line, a dashed dotted line, and a dashed double-dotted line. In the example of FIG. 10, the zone common to the behavior areas is represented as a region shaded with diagonal lines.

Figure 11:
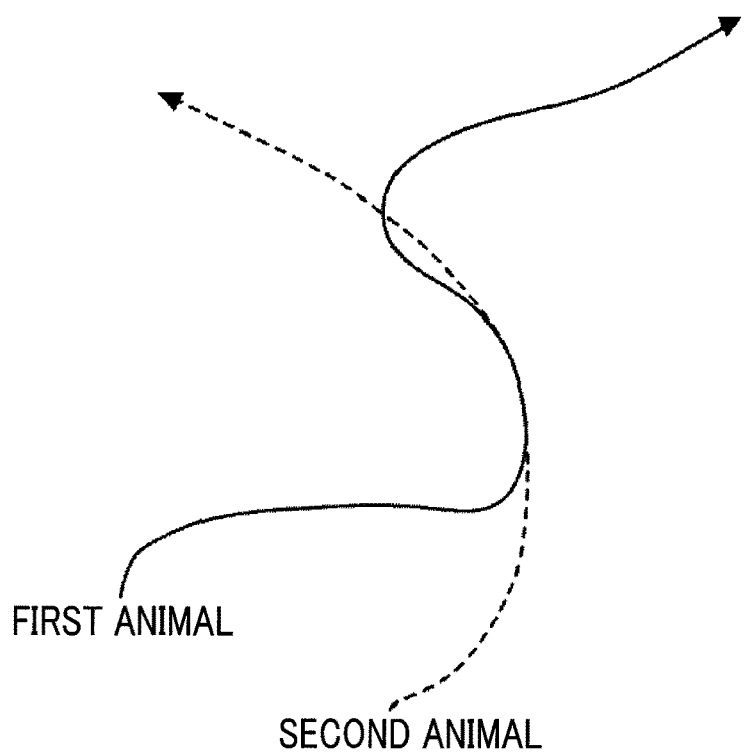
FIG. 11 is a diagram for describing an alarm notification process depending on a degree of overlapping of movement paths according to the modification example.
Figure 12:
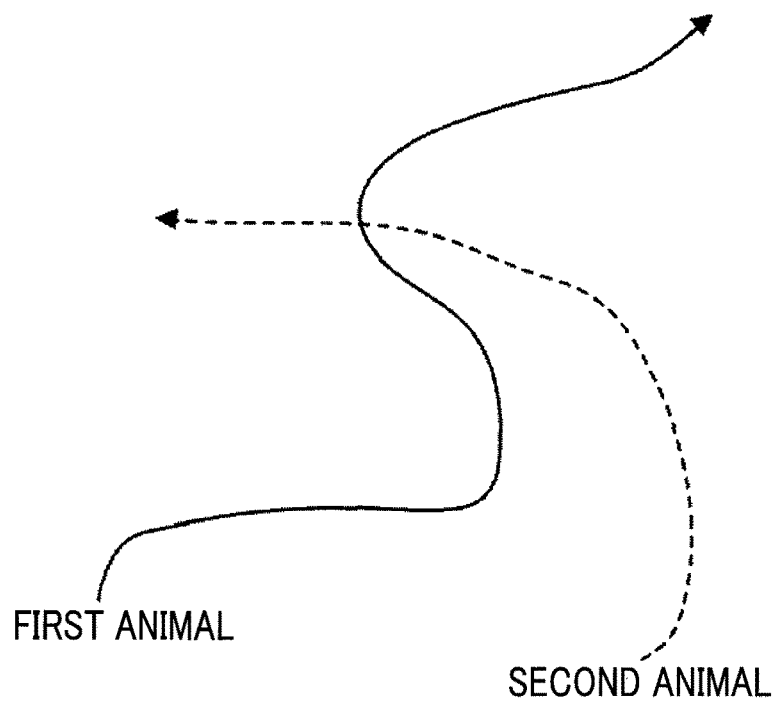
FIG. 12 is a diagram for describing the alarm notification process depending on the degree of overlapping of movement paths according to the modification example.

In the aforementioned embodiment, the notification unit 46 may notify of the alarm regarding the infection disease by changing the content of the alarm depending on a degree of overlapping (hereinafter, simply referred to as a "degree of overlapping") of a movement path of the first animal and a movement path of the second animal. An example of a specific alarm notification process in this case will be described with reference to FIGS. 11 and 12. A solid arrow in FIGS. 11 and 12 represents the movement path of the first animal indicated by a history of the positional information of the first animal after a timing when it is estimated that the first animal is infected with the infection disease. A broken arrow in FIGS. 11 and 12 represents the movement path of the second animal indicated by a history of the positional information of the second animal after a timing when it is estimated that the first animal is infected with the infection disease. As shown in FIGS. 11 and 12, the degree of overlapping in the example shown in FIG. 11 is higher than the degree of overlapping in the example shown in FIG. 12.

In a case where the degree of overlapping is in a state shown in FIG. 11, the notification unit 46 notifies of an alarm including a message indicating that "please, visit animal hospital.", for example. Meanwhile, in a case where the degree of overlapping is in a state shown in FIG. 12, the notification unit 46 notifies of an alarm including a message indicating that "please, consider visiting animal hospital.", for example. That is, the notification unit 46 notifies of a stronger alarm as the degree of overlapping becomes higher. As the degree of overlapping becomes higher, the second animal is more likely to be infected with the infection disease. Accordingly, the stronger alarm is notified as the animal is more likely to be infected with the infection disease, and thus, the owner is more likely to take countermeasure to suppress the spread of the infection disease. As a result, it is possible to further suppress the spread of the infection disease. In this form example, the notification unit 46 may notify the second owner of information indicating the degrees of overlapping shown in FIGS. 11 and 12. In this case, the information indicating the degrees of overlapping is also displayed in addition to the message of the alarm on the display unit of the terminal device 14 owned by the owner of the second animal.

Figure 13:
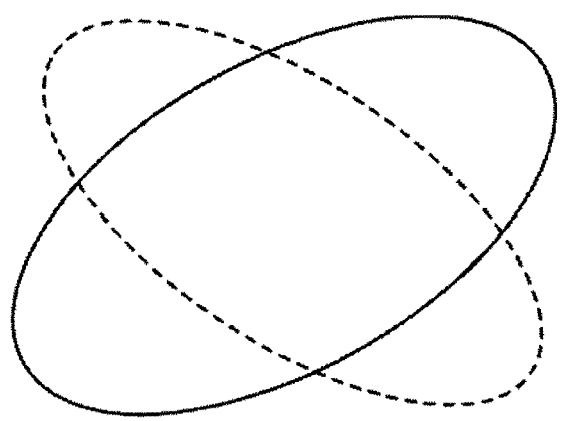
FIG. 13 is a diagram for describing the degree of overlapping of behavior areas corresponding to FIG. 11.
Figure 14:
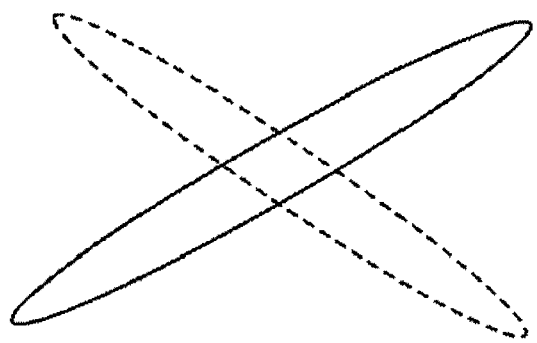
FIG. 14 is a diagram for describing the degree of overlapping of behavior areas corresponding to FIG. 12.

As the degree of overlapping in this form example, a degree of overlapping of a behavior area corresponding to the movement path of the first animal and a behavior area corresponding to the movement path of the second animal may be applied, as shown in FIGS. 13 and 14. In FIGS. 13 and 14, a solid line represents the behavior area of the first animal, and a broken line represents the behavior area of the second animal. The behavior area shown in FIG. 13 corresponds to the movement path shown in FIG. 11, and the behavior area shown in FIG. 14 corresponds to the movement path shown in FIG. 12.

Figure 15:
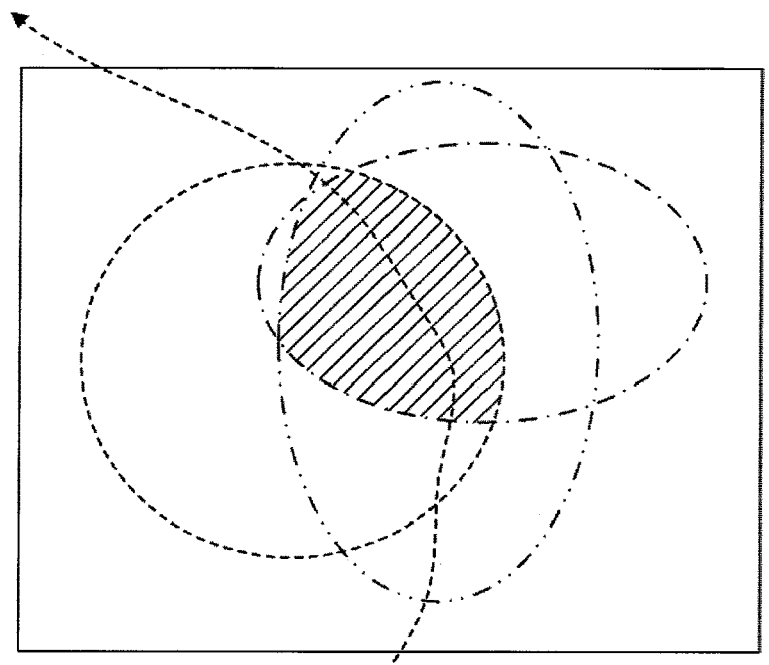
FIG. 15 is a diagram for describing the alarm notification process depending on the degree of overlapping of the movement paths according to the modification example.
Figure 16:
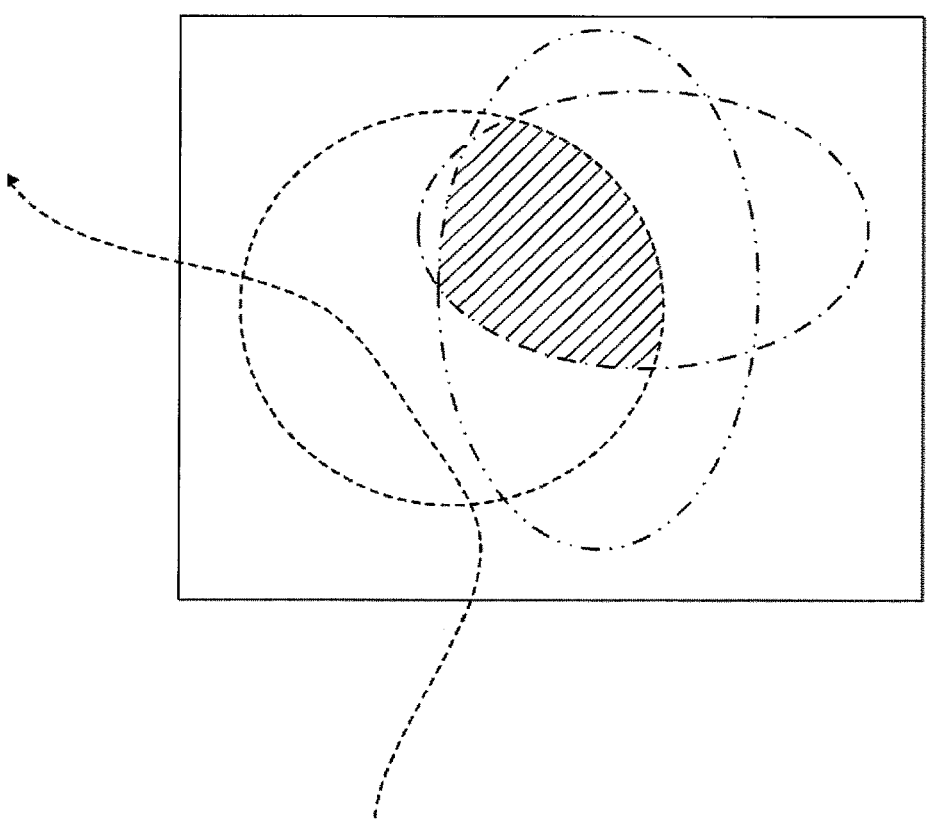
FIG. 16 is a diagram for describing the alarm notification process depending on the degree of overlapping of the movement paths according to the modification example.

As the degree of overlapping in this form example, a degree of overlapping of the zone common to the behavior areas shown in FIG. 10 and the movement path of the second animal may be applied. An example of the specific alarm notification process in this case will be described with reference to FIGS. 15 and 16. FIGS. 15 and 16 are diagrams in which a broken arrow representing the movement path of the second animal indicated by the history of the positional information of the second animal is added to the behavior area of the first animal shown in FIG. 10. As shown in FIGS.

15 and 16, a degree of overlapping in the example shown in FIG. 15 is higher than a degree of overlapping in the example shown in FIG. 16.

In this case, the notification unit 46 notifies of a stronger alarm in a case where the degree of overlapping is in the state shown in FIG. 15 than an alarm in a case where the degree of overlapping is in the state shown in FIG. 16. That is, the notification unit 46 notifies of a stronger alarm as the degree of overlapping becomes higher.

In the aforementioned embodiment, information regarding a family of the owner may be further stored in the owner information of the animal management table 32. In this case, the notification unit 46 may also transmit the alarm for the owner performed in step S18 or S20 of the alarm process shown in FIG. 7 to the family of the owner. In this case, a display screen shown in FIG. 8 or 9 is displayed on the display unit of the terminal device 14 owned by the family of the owner. In this form example, even in a case where the owner is away from home, the family at home can take countermeasures to suppress the spread of the infection disease to other animals. In a case where the countermeasures to suppress the spread of the infection disease in this case are completed, the terminal device 14 owned by the person who takes the countermeasures may transmit a message indicating that the countermeasures are completed to the terminal device 14 owned by the family.

In the embodiment, for example, various processors to be described below can be used as hardware structures of the processing units that perform various processes such as the acquisition unit 40, the specification unit 42, the determination unit 44, and the notification unit 46. As stated above, examples of various processors include a programmable logic device (PLD) such as a FPGA which is a processor of which a circuit configuration can be changed after being manufactured, a dedicated electric circuit such as an application specific integrated circuit (ASIC) which is a processor having a circuit configuration designed as a dedicated circuit in order to perform a specific process in addition to the CPU which is a general-purpose processor functioning as various processing units by executing software (program).

One processing unit may be constituted by one of these various processors, or may be constituted by a combination (for example, a combination of a plurality of FPGAs or a combination of the CPU and the FPGA) of the same kind or different kinds of two or more processors. Alternatively, the plurality of processing units may be constituted by one processor. Firstly, as the example in which the plurality of processing units is constituted by one processor, there is a form in which one processor is constituted by a combination of one or more CPUs and software and this processor functions as the plurality of processing units as represented by computers such as a client and a server. Secondly, there is a form in which a processor that implements the entire system function including the plurality of processing units by one integrated circuit (IC) chip as represented by a system on chip (SoC) is used. As stated above, various processing units are constituted as hardware structure by using one or more of various processors.

More specifically, an electric circuitry acquired by combining circuit elements such as semiconductor elements can be used as the hardware structure of these various processors.

Although the aspect in which the information processing program 30 is stored (installed) in advance in the storage unit 22 has been described in the embodiment, the present disclosure is not limited thereto. The information processing program 30 may be provided while being recorded in a recording medium such as a compact disc read only memory (CD-ROM), a digital versatile disc read only memory (DVD-ROM), and a universal serial bus (USB) memory. The information processing program 30 may be downloaded from an external device via a network.

What is claimed is:

1. An information processing apparatus comprising:
an acquisition unit that acquires information regarding an infection disease of a first animal infected with the infection disease;
a specification unit that specifies a second animal positioned within a behavior area of the first animal;
a determination unit that determines whether or not the infection disease of the first animal is likely to infect the second animal; and
a notification unit that notifies an owner of the second animal of an alarm regarding the infection disease in a case where it is determined that the infection disease of the first animal is likely to infect the second animal.

2. The information processing apparatus according to claim 1,
wherein the determination unit determines whether or not the infection disease of the first animal is likely to infect the second animal by determining whether or not a type of the second animal is a type of an animal that is likely to be infected with the infection disease of the first animal.

3. The information processing apparatus according to claim 1,
wherein, in a case where there is a plurality of the first animals, the specification unit specifies, as a zone in which there is an infection source of the infection disease, a zone common to the behavior areas of the plurality of first animals, and specifies, as the second animal, the animal positioned within the specified zone.

4. The information processing apparatus according to claim 1,
wherein the specification unit specifies the second animal positioned within the behavior area of the first animal during a lifetime of a virus of the infection disease of the first animal.

5. The information processing apparatus according to claim 1,
wherein the determination unit further determines whether or not the infection disease of the first animal is likely to infect human, and
in a case where it is further determined that the infection disease of the first animal is likely to infect human, the notification unit further notifies the owner of the second animal of an alarm indicating that the infection disease is likely to infect human.

6. The information processing apparatus according to claim 1,
wherein the notification unit notifies of the alarm regarding the infection disease by changing a content of the alarm depending on a degree of overlapping of a movement path of the first animal and a movement path of the second animal.

7. The information processing apparatus according to claim 1, wherein the notification unit notifies the owner of the second animal of the alarm regarding the infection disease, in a case in which the determination of the determination unit is a positive determination.

8. An information processing method which is executed by a computer, the method comprising:
acquiring information regarding an infection disease of a first animal infected with the infection disease;

specifying a second animal positioned within a behavior area of the first animal;

determining whether or not the infection disease of the first animal is likely to infect the second animal; and notifying an owner of the second animal of an alarm regarding the infection disease in a case where it is determined that the infection disease of the first animal is likely to infect the second animal.

9. The information processing method according to claim 8, wherein the owner of the second animal is notified of the alarm regarding the infection disease, in a case in which a result of the determining is a positive determination.

10. A non-transitory recording medium recording an information processing program causing a computer to execute processes of:

acquiring information regarding an infection disease of a first animal infected with the infection disease;

specifying a second animal positioned within a behavior area of the first animal;

determining whether or not the infection disease of the first animal is likely to infect the second animal; and notifying an owner of the second animal of an alarm regarding the infection disease in a case where it is determined that the infection disease of the first animal is likely to infect the second animal.

11. The non-transitory recording medium of claim 10, wherein the owner of the second animal is notified of the alarm regarding the infection disease, in a case in which a result of the determining is a positive determination is a positive determination.

* * * * *